(12) United States Patent
Wingler

(10) Patent No.: US 7,641,620 B2
(45) Date of Patent: Jan. 5, 2010

(54) ROTATABLE SAMPLING APPARATUS

(75) Inventor: Troy W. Wingler, Gosport, IN (US)

(73) Assignee: Vance Products Incorporated, Spencer, IN (US)

( * ) Notice: Subject to any disclaimer, the term of this patent is extended or adjusted under 35 U.S.C. 154(b) by 0 days.

(21) Appl. No.: 11/009,670

(22) Filed: Dec. 10, 2004

(65) Prior Publication Data
US 2005/0137500 A1 Jun. 23, 2005

Related U.S. Application Data

(60) Provisional application No. 60/532,398, filed on Dec. 23, 2003.

(51) Int. Cl.
*A61B 10/00* (2006.01)

(52) U.S. Cl. .................. 600/562; 604/238; 604/241

(58) Field of Classification Search ......... 600/573–584, 600/562–572; 604/167–168, 247, 280, 283–284, 604/905; 285/322, 921; 128/247, 349
See application file for complete search history.

(56) References Cited

U.S. PATENT DOCUMENTS

| | | | |
|---|---|---|---|
| 2,496,149 A * | 1/1950 | Cahenzli, Jr. ............ 285/332.2 |
| 2,755,801 A * | 7/1956 | Morando ................... 604/242 |
| 2,893,395 A * | 7/1959 | Buck .......................... 604/533 |
| 3,502,097 A * | 3/1970 | Muller ........................ 137/318 |
| 3,542,024 A * | 11/1970 | Burke ......................... 604/241 |
| 4,043,336 A * | 8/1977 | Kreb, III ..................... 600/578 |
| 4,046,479 A * | 9/1977 | Paley .......................... 403/306 |
| 4,156,435 A * | 5/1979 | Norton et al. .............. 137/240 |
| 4,187,848 A * | 2/1980 | Taylor ........................ 604/243 |
| 4,306,570 A * | 12/1981 | Matthews ................... 600/567 |
| 4,893,848 A * | 1/1990 | Melcher ..................... 285/258 |
| 5,066,286 A * | 11/1991 | Ryan .......................... 604/240 |
| 5,226,898 A * | 7/1993 | Gross ......................... 604/243 |
| 5,246,012 A * | 9/1993 | Strickland .................. 600/581 |
| 5,352,410 A | 10/1994 | Hansen et al. |
| 5,456,676 A * | 10/1995 | Nelson et al. .............. 604/533 |
| 5,509,911 A * | 4/1996 | Cottone et al. ............. 604/536 |
| 5,526,822 A * | 6/1996 | Burbank et al. ............ 600/567 |
| 5,575,778 A * | 11/1996 | Hardt et al. ................ 604/200 |
| 5,919,169 A * | 7/1999 | Grams et al. ............... 604/241 |
| 6,315,737 B1 * | 11/2001 | Skinner ...................... 600/566 |

(Continued)

FOREIGN PATENT DOCUMENTS

DE            532 192 C        8/1931

(Continued)

OTHER PUBLICATIONS

International Search Report including Written Opinion, dated Apr. 14, 2005 for PCT Application No. PCT/US2004/043757.

*Primary Examiner*—Max Hindenburg
*Assistant Examiner*—Rene Towa
(74) *Attorney, Agent, or Firm*—Brinks Hofer Gilson & Lione

(57) ABSTRACT

A sampling apparatus for taking a sample from the body of a patient is easily rotatable while the sample is being taken. This allows the physician to aspirate or draw the sample, rotating the sampling apparatus while holding stationary a syringe or other container for receiving the sample.

8 Claims, 4 Drawing Sheets

U.S. PATENT DOCUMENTS

| | | | |
|---|---|---|---|
| 6,344,033 B1 * | 2/2002 | Jepson et al. | 604/256 |
| 6,591,876 B2 * | 7/2003 | Safabash | 141/329 |
| 6,699,222 B1 * | 3/2004 | Jones et al. | 604/187 |
| 6,758,824 B1 * | 7/2004 | Miller et al. | 600/568 |
| 2004/0049162 A1 * | 3/2004 | Fisher | 604/240 |
| 2004/0106891 A1 * | 6/2004 | Langan et al. | 604/19 |
| 2004/0254538 A1 * | 12/2004 | Murphy et al. | 604/181 |
| 2005/0171504 A1 * | 8/2005 | Miller | 604/506 |

FOREIGN PATENT DOCUMENTS

| | | | |
|---|---|---|---|
| DE | 3102142 A1 * | 8/1982 | |
| EP | 0 029 126 A1 | 5/1981 | |

* cited by examiner

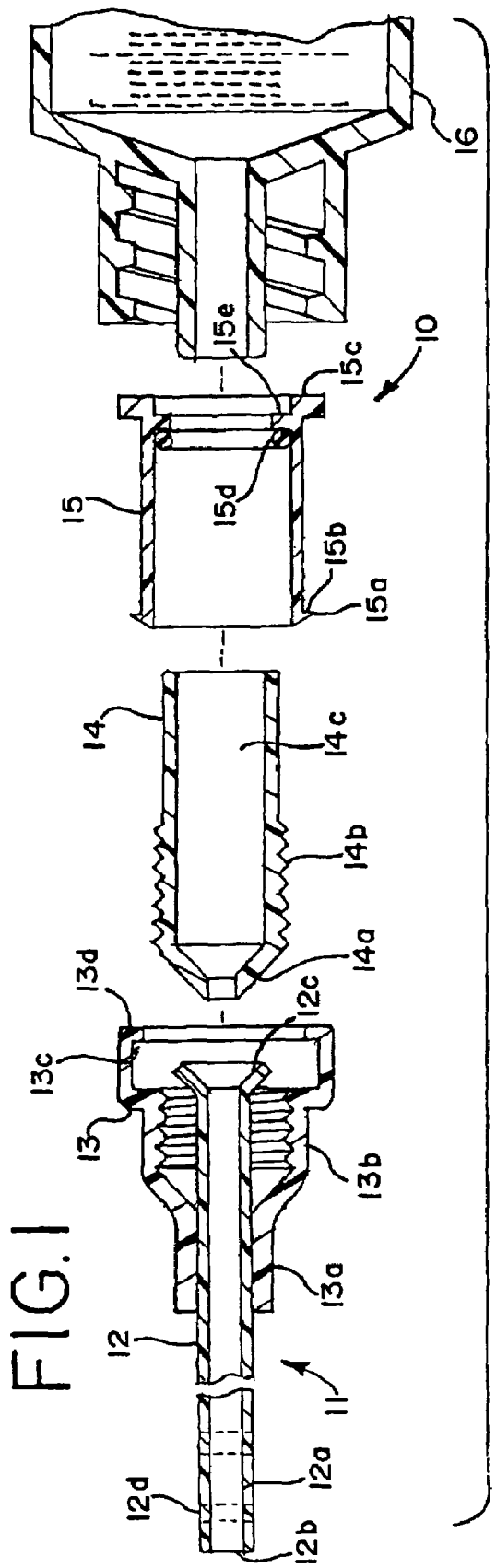
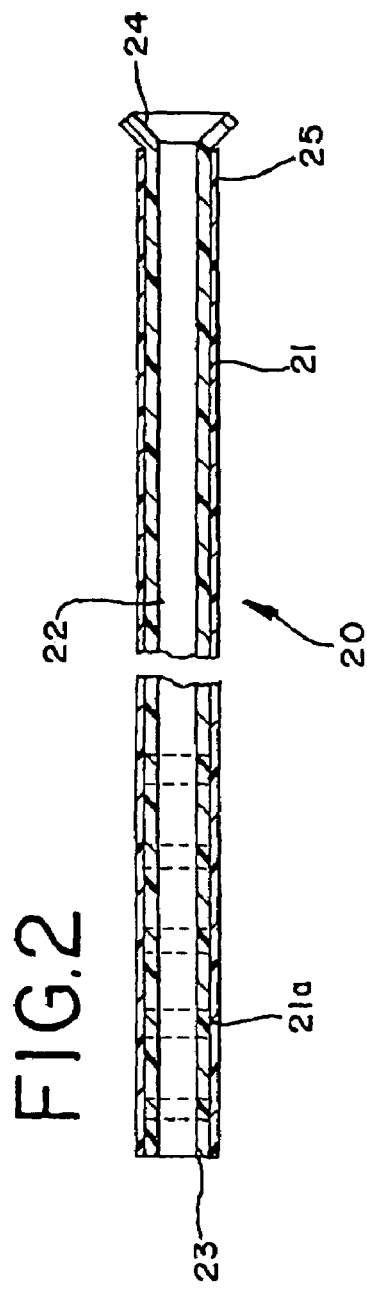

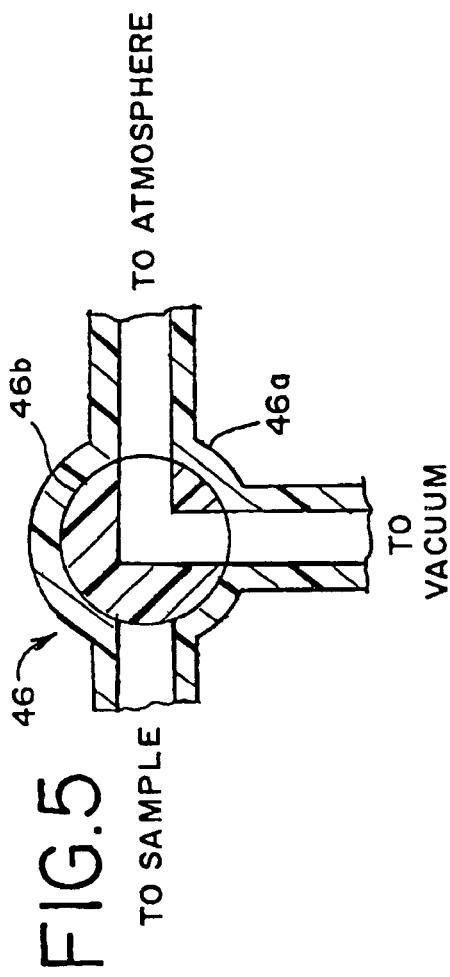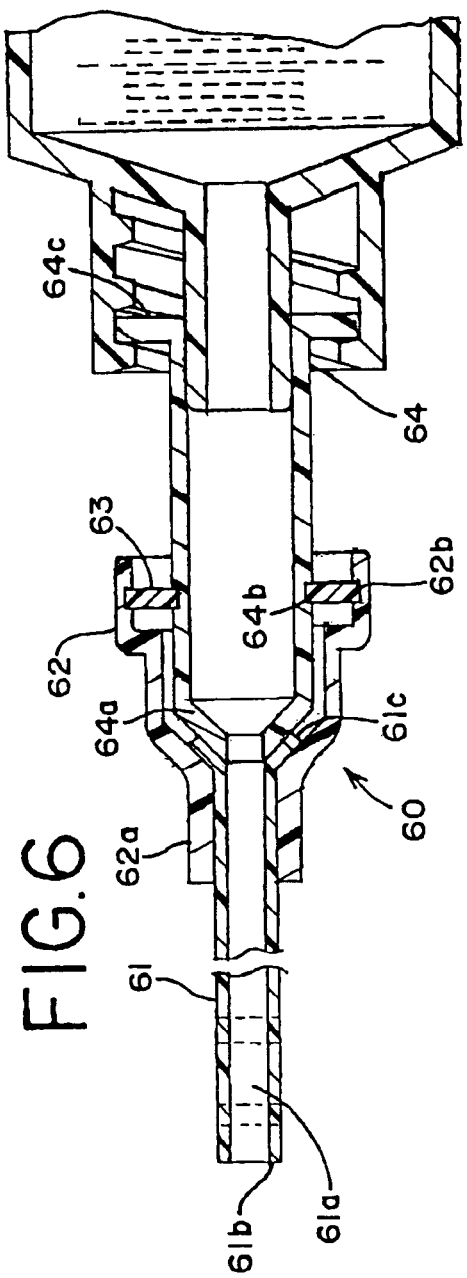

ROTATABLE SAMPLING APPARATUS

This application claims the benefit of the filing date under 35 U.S.C. § 119(e) of Provisional U.S. Patent Application Ser. No. 60/532,398, filed on Dec. 23, 2003, which is hereby incorporated by reference in its entirety.

FIELD OF THE INVENTION

The field of the invention is that of medical devices, and in particular that of devices that are able to remove samples from a body or to acquire samples from other specimens.

BACKGROUND

Medical devices that can remove samples from a body are used often. One type of device is fairly simple, amounting to a syringe with a sampling train and a thin tube to reach the sampling area. The tubing is typically very thin, so as to be very flexible and to reach into far areas of the body. The sampling train is typically little more than a connector to connect the tubing to a syringe. The syringe is then used both to provide suction to the tubing, and also to store the sample that is thus aspirated.

These devices are used to aspirate samples from a number of areas of the body that are not readily accessible. Included are esophageal samples, gastroenterological samples, urological samples, and samples from the vagina and uterus. One example is a procedure that is performed fairly frequently, a sampling of the endometrium of the uterus. In order to extract a sample, a physician must infiltrate the tubing into the desired area, ensuring that the tubing goes into the correct area of the body, and that no body tissues will be harmed by the sampling apparatus or by the aspiration of the sample. Once the physician is assured that the sampling tubing is placed properly, a sample is taken by aspiration. In order to take a good sample, the physician draws the plunger out of the syringe, causing aspiration at the distal end of the tubing. The physician must also rotate the syringe and plunger while aspirating, in order to insure that a representative and adequate sample is taken.

This procedure is very difficult to perform, requiring a great deal of dexterity and coordination, and the procedure is not always successful because of this difficulty. Thus, the procedure must sometimes be repeated, with all necessary steps re-taken to insure that the tubing is properly placed. A better procedure for aspirating samples is needed.

BRIEF SUMMARY

There are many ways to practice the invention. One aspect of the invention is a rotating apparatus for taking a biopsy sample including a portion of tubing, a fitting sealing with the tubing and further comprising a rotating seal, and a connector comprising a sealing surface and a connection for a receptacle for the biopsy sample.

Another aspect of the invention is a rotating apparatus for taking a sample. The apparatus comprises a portion of tubing, and a fitting sealing with the tubing and further comprising a rotating seal. The apparatus further comprises an adapter comprising a sealing surface and a connection.

Another aspect of the invention is a method of aspirating a biopsy sample. The method comprises connecting an apparatus for taking a sample to a receptacle for receiving the sample, the apparatus comprising a portion of tubing, a rotating fitting sealing with the tubing, and a connector or adapter sealing with the rotating fitting and having a connection. The method further comprises positioning the apparatus, and rotating the rotating fitting and tubing while aspirating the sample through the connection. The method also comprises collecting the sample.

There are many ways to practice the present invention, a few of which are shown in the following drawings and specification. The embodiments are not meant to limit the invention, but rather to describe and illustrate a few of the many ways that the present invention may be used.

BRIEF DESCRIPTION OF THE DRAWINGS

FIG. 1 is an exploded view of a first embodiment of a rotating apparatus used to take a biopsy sample from an endometrium of a uterus;

FIG. 2 is a view of a second tubing embodiment;

FIG. 5 is a closer view of one component of FIG. 4;

FIG. 6 is another embodiment of the invention; and

DETAILED DESCRIPTION OF THE DRAWINGS AND THE PRESENTLY PREFERRED EMBODIMENTS

Figure 3:
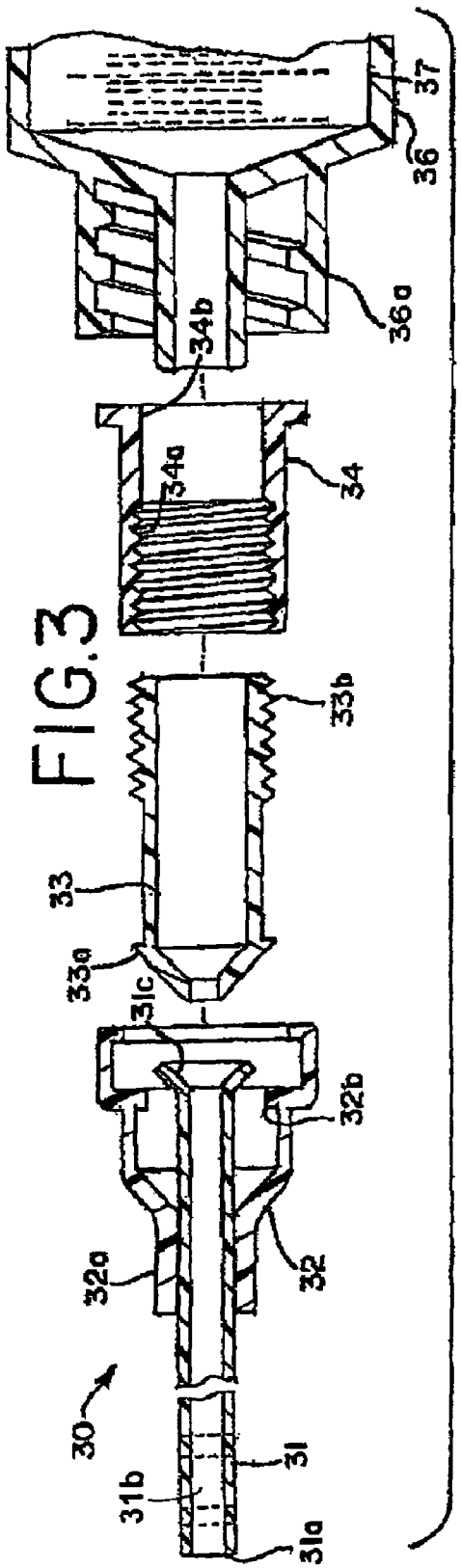
FIG. 3 is an exploded view of a second embodiment of a rotating apparatus.

An exploded view of a first embodiment of the sampling apparatus 10 is depicted in FIG. 1. The apparatus includes a distal rotating sampling portion 11, an optional intermediate portion 14, and a connector 15. As shown in FIG. 1, the sampling apparatus is preferably used with a syringe 16 to aspirate a sample. The sampling portion 11 includes tubing 12 for sampling and a rotating fitting 13 into which tubing 12 fits tightly. The tubing 12 preferably has a central lumen 12a and a soft, atraumatic distal end 12b, where the tubing will contact a portion of the patient's body to take the desired sample. The tubing preferably has distance markings 12d at the distal end and a flared end 12c at the proximal end.

Tubing 12 fits snugly into distal portion 13a of rotating fitting 13. The rotating fitting preferably also has internal threads 13b for mating with the optional intermediate portion 14. Following the threaded portion, the rotating fitting has a snap fit on its distal end including a void 13c for receiving a male snap fit portion from connector 15, and a lip 13d for securing connector 15. Lip 13d forms a sealing surface with the rear surface 15b of snap fit portion 15a. Connector 15 also includes a locking feature 15c such as a Luer lock feature, for securing to syringe 16. The Luer lock feature may be a male Luer lock feature or a female Luer lock feature on connector 15, while the syringe has the opposite, mating feature. Note also that the linear orientation of the component parts is slightly altered, and that when assembled, flared end 12c will seal against the inside of rotating fitting 13, on the angled surface between distal portion 13a and threads 13b.

Optional intermediate portion 14 includes a forward tapered portion 14a, preferably male threads 14b, and a central lumen 14c. Intermediate portion 14 is secured to rotating fitting 13 by threading the threaded portions together. The fittings are designed so that when intermediate portion 14 is threaded into rotating fitting 13, tapered portion 14a gently seals against tapered end 12c of sampling tubing 12. The three portions, constituting the rotating portion, are thus fitted together, tubing 12, rotating fitting 13, and intermediate portion 14, and will tend to rotate together. The three portions are internally sealed at the internal tapers, and the sample taken at distal end 12b will remain inside the central lumen of both tubing 12 and intermediate portion 14.

The assembly is completed when the rotating portion is assembled to connector 15 and then to a syringe. In this embodiment, the locking feature snap fits into the rotating portion by the snap fit features described above. Fitting 13 receives male snap fit portion 15a into void 13c and rotatably seals connector 15 at sealing surface 15b. Thus, even though connector 15 cannot rotate, because it is locked to the syringe or other receiving device, the sampling tube 12, rotating fitting 13, and intermediate portion 14 may all rotate. The sample is held within the central lumen of the tubing and the intermediate portion. The lengths of the parts described above are chosen so that the seals are tight and the fluid sampled remains within the desired portions until it reaches the syringe or other desired storage container. Connector 15 may also have a lip 15e and an O-ring 15d to seal against intermediate portion 14 to insure containment of the sample. The seal may be made by a washer or other sealing surface instead of O-ring 15d.

The sampling apparatus is assembled and is placed as desired into the patient. The physician aspirates the sample by pulling gently out the plunger of the syringe while rotating the rotating portion. The sample is thus aspirated into the tubing, through the sampling apparatus, and into the syringe. The combination of the rotatable fitting and the rotatable snap fit feature of the fitting and the connector allow for easy rotation of the rotating fitting, while not requiring the physician to also rotate the syringe.

The tubing used is preferably radiopaque, so that the physician may be sure of the placement of the tubing before the sampling procedure begins. Radiopacity may be imparted to the tubing by a number of techniques, including compounding the tubing material with barytes (barium sulfate), bismuth oxide, bismuth subcarbonate, and a number of other compounds. Radiopaque tubing is made from a large number of materials suitable for embodiments of the sampling apparatus, including polyethylene, polyurethane, and silicone. Radiopaque tubing is available from a number of manufacturers, including Extrusioneering, Inc., Temecula, Calif., and Qosina, Corp., Edgewood, N.Y.

If desired, the tubing may instead be echogenic, that is, visible under ultrasonic imaging. Tubing is typically made echogenic by applying a coating with a microporous surface structure, allowing for multiple reflections of the ultrasound energy and making the tubing "visible" in an ultrasound image. Other techniques to impart echogenicity may also be used. Tubing that is echogenic may be purchased commercially from a number of suppliers, including Diablo Sales, Danville, Calif., and STS Biopolymers, Henrietta, N.Y. Tubing with a coating that may be echogenic is depicted in FIG. 2. Sampling tubing 20 includes a tubing length 21, a central lumen 22, an atraumatic tip 23, a flared end 24, and a coating 25. Tubing 20 may also have markings 21a at the distal end, as shown, or at the proximal end, to aid the surgeon in determining the position of the tubing.

In addition to echogenic coatings, lubricious coatings may be applied. Tubing with a diameter of 9-10 Fr is preferred, the tubing having an outer diameter from about 0.066 inches (1.7 mm) to about 0.13 inches (3.0 mm). This apparatus allows a fair amount of freedom in the application of materials, so long as the materials do not stress or damage the body or the specimen from which a sample is being aspirated, and so long as there is no interaction or interference from the materials and the samples aspirated. As noted above, a number of materials may be suitable for the tubing itself. Soft tubing, in particular, is preferred for the sampling tubing.

The other components of the sampling apparatus may use a variety of materials for the applications. The rotating fitting is desirably harder than the tubing, so that there is a hard-on-soft seal, allowing the flared end of the soft tubing to lay against the distal portion of the rotating fitting. Suitable materials include polycarbonate, acetal, and fluoropolymers, such as Teflon®. Alternatively, a hard grade of polyethylene, such as high density polyethylene, may be used. If an adapter is used, preferably threaded into the rotating fitting, it need only be compatible with the fluid being sampled, and with the rotating fitting. Thus, almost any medically acceptable material may be used here also. Preferred materials include acetal, polycarbonate, and high density polyethylene. The connector, or portion that connects to a syringe or receptacle for holding the sample, may also be made from several differing materials. Acetal, high density polypropylene, polycarbonate, and a variety of other materials are suitable.

The embodiment of FIG. 1 is only one embodiment of the invention, which has many embodiments. A second embodiment of a sampling apparatus 30 is depicted in the exploded view of FIG. 3. In this embodiment, there is a length of tubing 31, a rotating fitting 32, an adapter 33, and an optional connector 34 for connecting to a syringe 36 and plunger 37. In this embodiment, tubing 31 includes an atraumatic distal tip 31a, a central lumen 31b, and preferably a flared end 31c. The flared end is not necessary for the proper functioning of any of the sampling apparatus embodiments. Given the design of the other components, such as the fit between the tubing and the rotating fitting, and the adapter and connector, it is highly unlikely that any leakage of sample or biopsy fluid would leak from the sampling apparatus. However, the flared end makes leakage even more unlikely and is prudently used to conserve what may be a limited amount of sample.

The components of the second embodiment also include a rotating fitting 32 with a sealing forward portion 32a that fits tightly with the tubing and prevents leakage. The rotating fitting also comprises a female snap fit feature 32b, that, as described above, includes a lip for providing a sealing surface and a void to accommodate the mating adapter 33. Adapter 33 includes a male snap fit 33a that fits into the female snap fit feature 32b of rotating fitting 32. Adapter 33 also includes a threaded portion 33b for connecting to connector 34. Optional connector 34 includes mating threads 34a and a connector 34b for connecting to a mating connection 36a on a syringe 36 or other container for the sample. Also depicted is the plunger 37 for operating the syringe 36. Sampling apparatus 30 is desirably used in connection with syringe 36 and plunger 37 to aspirate a sample.

Note that is possible to further modify the embodiment of FIG. 3 to simplify the sampling apparatus. Optional connector 34 is not needed if the threads 33b of the adapter are used to connect to either a second length of tubing or to connect directly to a receptacle for receiving the samples. In this modification, the container would have mating threads for threads 33b. Alternately, a short length of tubing could be used between the adapter and a container for receiving the aspirated sample.

Figure 4:
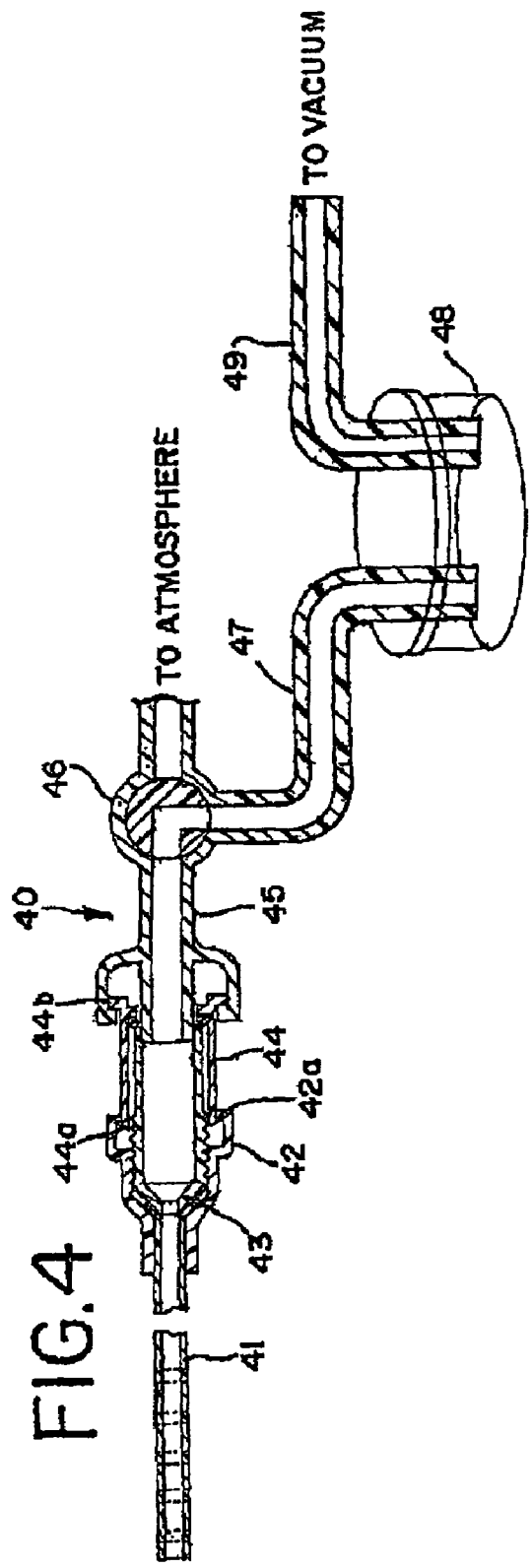
FIG. 4 is an exploded view of another embodiment of a rotating sampling apparatus.

While a syringe, as shown in FIGS. 1 and 3, is a very convenient way to use the sampling apparatus, it is not the only way that may be used with embodiments of the present invention. An alternative embodiment is depicted in FIGS. 4-5, in which a small sample jar or receptacle and a remote vacuum are used to aspirate a sample. In this embodiment, the suction necessary to aspirate the sample is provided by a remote source of vacuum (not shown) routed through tubing 47, 49 and a sample container 48. The sampling apparatus 40 includes a length of tubing 41 as previously described, rotating fitting 42 with female snap fitting 42a, an optional adapter 43, and a connector 44. Connector 44 includes a male snap fit connector 44a and a proximal end 44b. In this embodiment, proximal end 44b may be simply a length of plastic.

Other components that may be used with the sampling apparatus include tubing 45. Tubing 45 desirably fits over and seals the pathway with connector 44 and proximal end 44b. Tubing 45 also connects to a three way valve 46 for controlling the application of remote vacuum to the sampling apparatus. Three-way valve 46 connects to a sampling container 48 and to a remote vacuum (not shown) with tubing 47, 49 or other convenient connectors.

In use, the physician turns the three-way valve to a non-sampling position, in which the vacuum is not directed to the sampling apparatus before the vacuum is turned on or the connections between all parts is complete. Details of the three-way valve are shown in FIG. 5. Three way valve 46 includes a housing 46a with three ports as shown, and a stem 46b with only two ports, allowing the vacuum to connect only with the sampling train or to atmosphere, but not both. Other valves and other connections may also be used.

Another sealing arrangement that may be used in a rotating sampler according to the present invention is depicted in FIG. 6. The sampler apparatus 60 may be used for gathering biopsy samples or for gathering other samples of interest. The apparatus includes a length of soft tubing 61, a rotating fitting 62, a seal 63, and an adapter 64 that includes a connection. The soft tubing and the rotating fitting rotate, while the adapter is firmly connected, either to a receptacle for receiving the sample, or to tubing or other plumbing leading to a receptacle. The seal may be stationary or may rotate.

Tubing 61 includes a central lumen 61a, an atraumatic distal or sampling end 61b, and a flared proximal end 61c. The rotating fitting includes a forward portion 62a that seals against soft tubing 61 and also includes a notch or sealing surface 62b in the proximal portion for accommodating seal ring 63. Seal 63 may be a flat polymeric or elastomeric washer, or may be an O-ring or other flexible seal such as a packing gland. Adapter 64 has a graduated proximal end 64a for urging tapered end 61c against the rotating seal, and also has a notch or sealing surface 64b for accommodating seal 63. There is also a male Luer lock connector 64c for connecting to a syringe or other receptacle for providing suction and depositing the sample.

In using this embodiment, tubing 61 and rotating fitting 62 rotate, while adapter 64 is stationary. Seal 63 may rotate or may be stationary. Seal 63 may be any medically acceptable grade of preferably soft elastomer or plastic, such as silicone, polyurethane, or polypropylene, for a low coefficient of friction from a soft-on-hard seal. Alternatively, harder plastics, with a low coefficient of friction may also be used for a hard-on-hard seal. The seal should not shed or add particles or dust to the sample as a result of rubbing on its surface, and thus non-filled grades are preferred. Suitable materials may include almost any fluoropolymer, such as Teflon®, polycarbonate, harder grades of urethane, acetal, and high-density polyethylene.

As noted above, the rotating sampling apparatus is expected to find use in a wide variety of sampling procedures, including urological procedures, biliary procedures, esophageal procedures and procedures for acquiring samples from the vagina and uterus, as well as gastroenterological samples. The details and the materials of the construction or composition of the various elements of the rotating sampling device and devices using the rotating sampler not otherwise disclosed are not believed to be critical to the achievement of the advantages of the present invention, so long as the components seal sufficiently to obtain and preserve the sample, and do not interfere with the sample.

Figure 7:
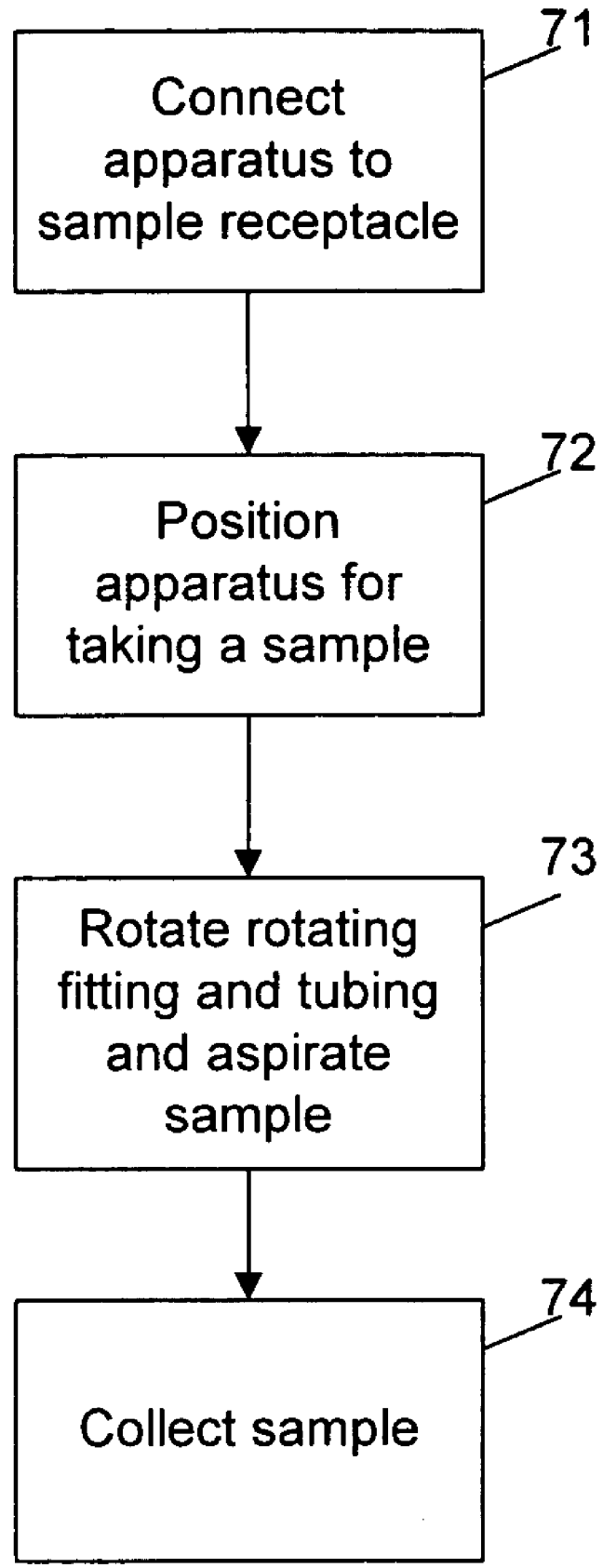
FIG. 7 is a flowchart depicting a method of practicing the invention.

A method of using the sampling apparatus is depicted in the flowchart of FIG. 7. The method includes several steps, of which the first step 71 may comprise connecting an embodiment of the sampling apparatus as discussed above to a receptacle for providing aspiration and collecting the sample. The next step 72 is to position the apparatus in a position for taking a sample, using radiographic or ultrasonic methods if necessary. The next step 73 is to rotate the sampling apparatus, the sampling tubing and the rotating fitting, while aspirating the sample. Finally, the sample is collected 74 for analysis or measurement. Other techniques or methods may used in employing the rotating sampling apparatus, including a different sequence of the first two steps of this method.

A snap fit connection with a seal has been made because this connection allows reasonable sealing along with some ability to rotate. While most of the snap fits are shown with a female connection on the rotating portion, the rotating sampling apparatus may be made with a male snap fit feature on the rotating portion and a matching female snap fit on the connecting portion, that is, the part that does not rotate. It is also possible to make connections with other seals, such as sliding seals with O-rings or washers, without a snap fit connection. These additional embodiments are understood to be well within the ability of one having skill in the art, in view of the present disclosure. The following claims therefore, are meant to be illuminating rather than limiting. It is therefore intended that the foregoing detailed description be regarded as illustrative rather than limiting, and that it be understood that it is the following claims, including all equivalents, that are intended to define the spirit and scope of this invention.

What is claimed is:

1. An adapter assembly comprising:
   a sample receptacle including a distal portion having a locking portion;
   a connector with a lumen defined therethrough including a proximal portion having a locking portion to engage the locking portion of the sample receptacle and an internal lip extending radially into the lumen, and a distal portion having a first surface;
   an adapter including a proximal portion and a threaded portion, wherein the proximal portion of the adapter is insertably disposed within the lumen of the connector and forms a sealed connection between the lip and an outer surface of the adapter, wherein the adapter is rotatable with respect to the internal lip of the connector while maintaining the sealed connection;
   a fitting including a proximal portion having a second surface to form a sealed connection, wherein the second surface is rotatable with respect to the first surface of the connector while maintaining the sealed connection, and a threaded portion to engage the threaded portion of the adapter; and
   a tube including a proximal portion attached to the fitting and a distal portion having an atraumatic tip.

2. The medical device of claim 1 wherein:
   the adapter includes a distal portion having a tapered end, and the fitting includes a distal portion having a tapered end.

3. The medical device of claim 1 wherein:
   the first surface is proximal facing, and the second surface is a lip contained within the fitting.

4. The medical device of claim 1 further comprising an O-ring positioned between the internal lip of the connector and the proximal portion of the adapter that forms a sealed connection that is rotatable with the internal lip of the connector with the proximal portion of the adapter.

5. An adapter assembly comprising:
   a sample receptacle including a distal portion having a locking portion;
   a connector including a proximal portion having a locking portion to engage the locking portion of the sample receptacle and an internal lip extending radially into a lumen disposed through the connector, and a distal portion having a first surface;
   an adapter including a proximal portion and a threaded portion, wherein the proximal portion of the adapter is insertably disposed within the lumen of the connector and forms a sealed connection between the lip and an outer surface of the adapter, wherein the adapter is rotatable with respect to the internal lip of the connector;
   a fitting including a proximal portion having a second surface to form a sealed connection; wherein the second surface is rotatable with respect to the first surface of the connector, and a threaded portion to engage the threaded portion of the adapter;
   a tube including a proximal portion attached to the fitting and a distal portion having an atraumatic tip.

6. The medical device of claim 5 wherein:
   the adapter includes a distal portion having a tapered end, and the fitting includes a distal portion having a tapered end.

7. The medical device of claim 5 wherein:
   the first surface is proximal facing, and the second surface is a lip contained within the fitting.

8. The medical device of claim 5, further comprising
   an O-ring positioned between the internal lip of the connector and the proximal portion of the adapter that forms a sealed connection that is rotatable with the internal lip of the connector with the proximal portion of the adapter.

\* \* \* \* \*

UNITED STATES PATENT AND TRADEMARK OFFICE
CERTIFICATE OF CORRECTION

PATENT NO. : 7,641,620 B2
APPLICATION NO. : 11/009670
DATED : January 5, 2010
INVENTOR(S) : Troy W. Wingler It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 74 days.

Signed and Sealed this

Sixteenth Day of November, 2010

David J. Kappos
*Director of the United States Patent and Trademark Office*